United States Patent [19]

Lipari

[11] 4,383,992

[45] May 17, 1983

[54] WATER-SOLUBLE STEROID COMPOUNDS

[76] Inventor: John M. Lipari, 1616 Kuiper La., Racine, Wis. 53406

[21] Appl. No.: 346,501

[22] Filed: Feb. 8, 1982

[51] Int. Cl.³ .............................................. A61K 31/56
[52] U.S. Cl. .................................. 424/238; 424/243;
260/239.5; 260/397.45
[58] Field of Search ............................ 424/243, 238; 260/397.45, 239.5

[56] References Cited

U.S. PATENT DOCUMENTS 3,079,410  2/1963  Fritsch et al. .................. 260/397.45

Primary Examiner—Elbert L. Roberts
Attorney, Agent, or Firm—Michael, Best & Friedrich

[57] ABSTRACT

Beta-cyclodextrin forms a water-soluble complex or inclusion compound with steroid compounds having a molecular structure smaller than the interior cavity in the doughnut-shaped molecular structure of beta-cyclodextrin. The resulting inclusion compounds can be used for a variety of applications including aqueous topical ophthalmic preparations and topical dermatological ointments.

10 Claims, No Drawings

WATER-SOLUBLE STEROID COMPOUNDS

BACKGROUND OF THE INVENTION

This invention relates to water soluble complexes or inclusion compounds of steroid compounds and use of same in pharmaceutical preparations.

Various steroid compounds are used in aqueous mediums, topical ointments and the like as pharmaceutical preparations for treating eye and skin disorders. Steroid compounds generally are substantially insoluble in water unless in the form of a salt. Consequently, when used in an aqueous medium, other additives are required to assist in maintaining the steroid compound in suspension. Aqueous suspensions containing steroid compounds which are not a salt or various esters usually must be shaken before use in order to obtain a uniform dispersion of the steroid compound and thereby insure that an accurate dosage is administered.

An example of such preparations are topical ophthalmic suspensions containing a corticosteroid, such as prednisolone acetate, dexamethasone and hydrocortisone acetate, and used for treatment of ocular inflammation. The patient must follow a dosage schedule and shake the bottle to fully suspend the corticosteroid so that the full dosage is delivered to the eye. Even though the label usually includes specific instructions to shake the bottle well before using, patients usually do not shake the bottle at all or shake it only a few times. In a study of commercially available corticosteroid suspensions reported in *Amer. J. of Opthal.*, 87:210–214 (1979), it was observed that, without shaking up to 15 times, concentrations ranging from less than 29% up to less 61% of the maximum concentration of the drug would be delivered to the eye. Thus, an inadequate dosage would be administered under ordinary condition of use.

During long term storage, steroid compounds tend to settle to the bottom of the bottle and become caked. In some cases the steroid compound and/or solid additives in the preparation deposit in the bottle tip and plug it so that the preparation cannot be squeezed out without first unplugging the tip with a needle or the like.

SUMMARY OF THE INVENTION

One of the objects of the invention is to provide water soluble steroid compounds and a method for making same.

Another object of the invention is to provide pharmaceutical preparations containing a water soluble inclusions compounds of one or more steroid compounds.

A further object of the invention is to provide a stable topical opthtalmic preparation including a steroid compound dissolved in an aqueous medium and a method for preparing same.

Other objects, aspects and advantages of the invention will become apparent to those skilled in the art upon reviewing the following detailed description and the appended claims.

It has been found that beta-cyclodextrin forms water-soluble complexes or inclusion compounds with steroid compounds, including corticosteroids, androgens, anabolic steroids, estrogens and progestagens, having a molecular structure smaller than the interior cavity of the doughnut-shaped molecular structure of beta-cyclodextrin. The resulting steroid compound: beta-cyclodextrin complex or inclusion compound readily dissolves in water to form a true solution. The complex or inclusion compound can be isolated from the solution in which it is formed for later use. Alternately, it can be formed by adding beta-cyclodextrin and one or more steroid compounds, preferably at a molar ratio of 1:1 or less, to an aqueous medium suitable for the end use and then diluting the resulting solution to obtain the desired concentration of the steroid compound(s).

DESCRIPTION OF THE PREFERRED EMBODIMENT

Beta-cyclodextrin is a cyclic polymer containing seven D-glucose units and is produced by reaction of *Bacillus macerans* amylase on starch. It has a molecular weight of 1135 and a doughnut-shaped molecular structure including an interior cavity having a diameter of approximately 7.5 Angstroms. The interior of the cavity consists largely of uniformly spaced bridging acetal oxygen atoms. One end of the cavity is edged with —$CH_2OH$ groups (one per glucose unit) and the other rim is edged with secondary —CHOH groups. The cavity contains water molecules hydrogen bonded to the interior oxygen atoms.

While the combination mechanism is not completely understood, it appears that steroid compounds having a molecular structure smaller than the cavity of beta-cyclodextrin enter the cavity, undergo a non-covalent interaction with the atoms lining and rimming the cavity and become complexed therewith to form an inclusion compound. Upon complexing with beta-cyclodextrin, steroid compounds which are substantially insoluble in water become readily soluble in water at room temperature to form a true solution. It has been found that alpha-cyclodextrin does not form water soluble complexes with most steroid compounds.

Various steroid compounds, including corticosteroids, androgens, anabolic steroids, estrogens and progestagens, having a molecular structure small enough to fit into the internal cavity of beta-cyclodextrin can be used to form water soluble complexes or inclusions compounds. The presently preferred steroid compounds can be represented but not limited to the following general chemical structure:

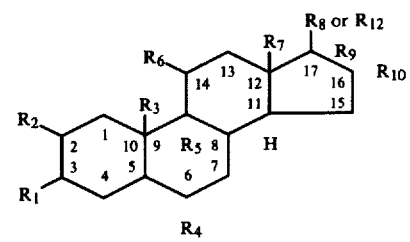

wherein $R_1$ is H, =O, OH, $OCH_3$ $OR_{11}$, or bridged with $R_2$

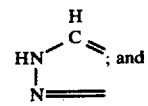; and $R_2$ is H, $CHOR_{11}$ or bridged with $R_1$ as noted above;
$R_3$ is H or $CH_3$;
$R_4$ is H, $CH_3$, F, Cl, or Br;
$R_5$ is H, F, Cl, or Br;
$R_6$ is H, =O, or $OR_{11}$
$R_7$ is H, $CH_3$ or $C_2H_5$;

$R_8$ is OH, =O, C≡CH, $R_{11}$, —$OR_{11}$ or
$R_9$ is H, OH, $CH_3$, $C_2H_5$, C≡CH, $OR_{11}$ or bridged with $R_{10}$ as

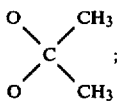

$R_{10}$ is H, $CH_3$, or $OR_{11}$;
$R_{11}$ is H, or

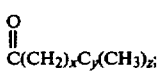

$R_{12}$ is

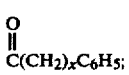

x is O or a positive integer of 1–10;
y is O or a positive integer of at least 1;
z is a positive integer of 1–3; and
the dotted lines indicate the alternate positions of the double bond.

While steroid compounds in each of the above classes can differ considerably, they usually have some common characteristics. When the steroid compound is a corticosteroid, usually $R_1$ is =O, $R_2$ is H, both $R_3$ and $R_7$ are $CH_3$, and the double bond is between the 4 and 5 positions. When the steroid compound is an androgen or anabolic steroid, usually $R_1$ is =O or bridged with $R_2$ as noted, $R_2$ is H, both $R_3$ and $R_7$ are $CH_3$, $R_8$ is OH and the double bond is between the 4 and 5 positions. When the steroid compound is an estrogen, usually $R_2$, $R_3$, $R_6$ and $R_{10}$ are H and there are three double bonds between the 1 and 2, the 3 and 4 and the 5 and 10 positions. Progestagens are much like estrogens except they usually have only a single double bond between the 4 and 5 positions or the 5 and 10 positions.

The inclusions compounds of the invention are readily soluble in water and form true solutions even through the steroid compounds are not salts or esters. This capability of readily dissolving in water to form a true solution provides several advantages. When used in an aqueous medium of topical opthalmic preparations for treating ocular inflammation, an accurate dosage can be delivered without shaking the bottle and plugging of the bottle tip by settled particles is minimized. The solution is substantially more stable thermodynamically, thereby minimizing settling and caking of the steroid compound on the bottom of the bottle. Only an unbound or free steroid compound is physiologically active. Thus, the complexed steroid compound must dissociate before it can interact with the biological receptors of the eye, thereby possibly providing a sustained release effect of the steroid compound. Although not yet verified, it is believed that the use of beta-cyclodextrin produces an increased partitioning of the steroid compound into the cornea with an increased therapeutic response.

Representative suitable corticosteroids include:
9-Fluoro-11β,17,21-trihydroxy-16α-methylpregna-1,4-diene-3,20-dione (dexamethasone);
11β,17,21-Trihydroxypregna-1,4-diene-3,20-dione acetate (prednisolone acetate);
17α,21-dihydroxy-4-pregnene-3,11,20-trione;
Desonide;
Desoxycorticosterone;
9α-Fluoro-11β,17α,21-trihydroxy-4-pregnene-3,20-dione;
6α,9α-Difluoro-11β,17α,21-trihydroxy-16α-methyl-pregna-1,4-diene-3,20-dione
6α,9α-Difluoro-11β,16α,17,21-tetrahydroxypregna-1,4-diene-3,20-dione cyclic 16,17-acetal with acetone;
Fluocinonide;
9α-Fluoro-11β,17α-dihydroxy-6α-methylpregna-1,4-diene-3,20-dione
6α-Fluoro-11β,17α,21-trihydroxypregna-1,4-diene-3,20-dione;
Flurandrenolide;
11β,17α,21-Trihydroxy-6α-methyl-1,4-pregnadiene-3,20-dione;
6α-Fluoro-11β,17α,21-trihydroxy-16α-methyl-1,4-pregnadiene-3,20-dione;
11β,17,21-Trihydroxypregna-1,4-diene-3,20-dione (hydrocortisone);
17α,21-Dihydroxypregna-1,4-diene-3,11,20-trione;
9-Fluoro-11β,16α,17,21-tetraphydroxypregna-1,4-diene-3,20-dione;
and any other corticosteroids having a similar chemical structure.

Suitable androgens and anabolic steroids include:
9α-Fluoro-11β,17β-dihydroxy-17α-methyl-4-androsten-3-one;
17β-Hydroxy-17-methylandrost-4-en-3-one;
17β-Hydroxy-4-androsten-3-one;
17β-Ethylestr-4-en-17β-ol;
17β-Hydroxy-17α-methylandrosta-1,4-diene-3-one;
17β-Hydroxyestr-4-en-3-one;
17β-Hydroxy-17-methyl-2-oxa-5α-androstan-3-one;
17β-Hydroxy-2-(hydroxymethylene)-17-methyl-5α-androstan-3-one;
1,2,3,3α,3β,4,5,5α,6,8,10,10α,10β,11,12,12α-Hexadecahydro-1,10α,12α-trimethylcyclopenta(7,8)-phenanthro(2,3-c)pyrazol-1-ol;
17β-Hydroxy-5α-androstan-3-one; and any other androgen
and anabolic steroids having a similar chemical structure.

Representative examples of suitable estrogens include:
1,3,5-Estratriene-3,17α-diol;
3-Hydroxyestra-1,3,5(10)-trien-17-one;
3-Methoxy-19-nor-17α-pregna-1,3,5(10)-trien-20-yn-17-ol;
and any other estrogens having a similar chemical structure.

Representative examples of suitable progestagens include:
Delta4-Pregnene-3,20-dione; 17-Hydroxypregna-4-ene-3,20-dione;
17-Hydroxy-6α-methylpregna-4-ene-3,20-dione;
10α-Pregna-4,6-diene-3,20-dione;
17α-Hydroxy-6-methylpregna-4,6-diene-3,20-dione acetate;
17α-ethynyl-17β-hydroxyl-4-androsten-3-one;
17-Hydroxy-19-nor-17α-pregn-4-en-20-yn-3-one;
17-Hydroxy-19-nor-17α-pregn-5(10)-en-20-yn-3-one;

6α-Methyl-17-(1-propynyl)testosterone;
19-Nor-17α-pregn-4-en-20-yne-3β,17-diol;
and any other progestagens having a similar chemical structure.

The inclusion compounds of the invention are prepared by first adding a sufficient amount of beta-cyclodextrin to an aqueous solution, preferably containing a small amount of a dispersing agent such as hydroxypropylmethylcellulose, to yield a solution saturated with respect to beta-cyclodextrin and agitating the resulting mixture for a sufficient time to obtain complete equilibrium between soluble and insoluble beta-cyclodextrin. The steroid compound to be complexed is admixed with the resulting solution to form a water-soluble inclusion compound. The amount of the steroid compound added to the solution can be up to a molar ratio to beta-cyclodextrin of about 1:1. Amounts of the steroid compound yielding molar ratios greater than about 1:1 usually produces little or no additional complexing. Best results generally are obtained by using a slight excess of beta-cyclodextrin in the complex-forming solution. The dissolved inclusion compound can be isolated from the aqueous medium for later use in a suitable manner, such as by evaporation or the like.

Aqueous pharmaceutical preparations, such a topical ophthalmic solution for treating ocular inflammation can be prepared without isolating the complex from the medium in which it is formed. This is accomplished by adding to an aqueous medium containing beta-cyclodextrin a desired steroid compound (e.g., prednisolone acetate, dexamethasone hydrocortisone, etc. for topical ophthalmic preparations), preferably at a molar ratio of about 1:1 or less, so that all, or substantially all, the steroid compound is complexed. A sufficient amount of water is then added to the resulting solution to obtain the desired concentration of the steroid compound which is effective for the end application of the ophthalmic solution. For such ophthalmic solutions the concentration of the inclusion compound usually is about 0.1 to about 1.0 volume %.

If desired, two or more different steroid compounds having a molecular structure smaller than the internal cavity in beta-cyclodextrin can be complexed in the same aqueous medium. The total molar ratio of the steroid compounds to beta-cyclodextrin preferably should be about 1:1 or less.

The inclusion compounds of steroids can be used for a variety of applications where the water solubility and/or the sustained release characteristic might be advantageous. The inclusion compounds can be mixed with various conventional, non-toxic carriers used in the preparation of different types of pharmaceutical compositions. For example, a hydrocortisone: beta-cyclodextrin inclusion compound, or a mixture of two or more suitable steroid: beta-cyclodextrin inclusion compounds can be used in place of the 1-dehydrocortisone used in the various pharmaceutical compositions (e.g., subcutaneous, intramuscular and intraarticular injections, nasal sprays, ophthalmic and dermatological ointments, topical creams, and topical ophthalmic solutions) disclosed in Examples C through Q in U.S. Pat. No. 3,134,718, which patent is incorporated herein by reference. Since the inclusion compounds of the invention are water soluble, the compositions disclosed in Examples C, K, L, M and N in that patent can be made as a solution instead of a suspension, in which case some or all of the dispersing agent(s) can be omitted. Also, for the ointments and topical creams disclosed in Examples O and P of that patent, the inclusion compounds can be dissolved in water prior to adding the other ingredients, thereby insuring uniform dispersion of the steroid compound in the final composition without special mixing procedures.

The amount of an inclusion compound, or mixture of two or more inclusion compounds, used in any particular pharmaceutical composition is that which will provide the desired therapeutic response.

Without further elaboration, it is believed that one skilled in the art can, using the preceeding description, utilize the present invention to its fullest extent. The following examples are presented to exemplify the preferred embodiments of the invention and should not be construed as limitations thereof.

EXAMPLE 1

5,000 mg of hydroxypropylmethylcellulose is mixed with 1,000 ml of distilled water in a container to obtain a 0.5% solution of hydroxypropylmethylcellulose (Solution No. 1). A sufficient amount (approximately 20 gm) of beta-cyclodextrin is added to Solution No. 1 at room temperature to yield a saturated solution (Solution No. 2) with respect to beta-cyclodextrin. Solution No. 2 is agitated for 24 hours to insure complete equilibrium between soluble and insoluble beta-cyclodextrin. 120 mg of prednisolone acetate is added to and dispersed in 90 ml of Solution No. 2 at room temperature. As the prednisolone acetate: beta-cyclodextrin inclusion compound is formed, it goes into solution. Sufficient distilled water is added to Solution No. 2 to bring the final volume to 100 ml and produce a topical ophthalmic solution containing 0.12% prednisolone acetate (as prednisolone acetate) for treating ocular inflammation.

Similar results have been obtained with dexamethasone and hydrocortisone.

EXAMPLE 2

120 mg of alpha-cyclodextrin was added to 5 ml of an aqueous suspension of dexamethasone at room temperature. Even though the resulting mixture was agitated for several minutes, the dexamethasone did not dissolve and remained in suspension. Similar results have been obtained with a variety of other steroid compounds found to form water-soluble complexes with beta-cyclodextrin.

The above tests results, demonstrate that only beta-cyclodextrin will form water-soluble complexes or incluson compounds with steroid compounds.

From the foregoing description, one skilled in the art can easily ascertain the essential characteristics of the invention and, without departing from the spirit and scope thereof, make various changes and modifications to adapt it to various usages.

We claim:

1. A water-soluble inclusion compound formed by complexing beta-cyclodextrin with a steroid compound having a molecular structure smaller than the inside dimension of the internal cavity of beta-cyclodextrin.

2. A water-soluble inclusion compound according to claim 1 wherein said steroid has the following general chemical structure:

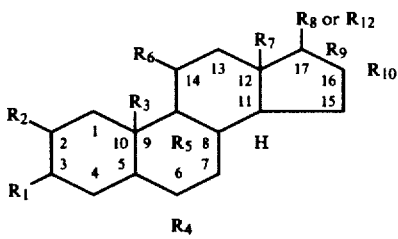

wherein $R_1$ is H, =O, OH, $OCH_3$ $OR_{11}$, or bridged with $R_2$

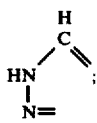

$R_2$ is H, $CHOR_{11}$ or bridged with $R_1$ as noted above;

$R_3$ is H or $CH_3$;

$R_4$ is H, $CH_3$, F, Cl, or Br;

$R_5$ is H, F, Cl, or Br;

$R_6$ is H, =O, or $OR_{11}$ $R_7$ is H, $CH_3$ or $C_2H_5$;

$R_8$ is OH, =O, C≡CH, $R_{11}$, $-OR_{11}$ or

$R_9$ is H, OH, $CH_3$, $C_2H_5$, C≡CH, $OR_{11}$ or bridged with $R_{10}$ as

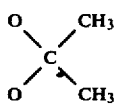

$R_{10}$ is H, $CH_3$, or $OR_{11}$;

$R_{11}$ is H, or

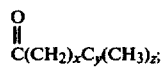

$R_{12}$ is

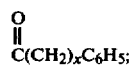

x is O or a positive integer of 1–10;

y is O or a positive integer of at least 1;

z is a positive integer of 1–3; and the dotted lines indicate the alternate positions of the double bond.

3. A water-soluble inclusion compound according to claim 2 wherein said steroid compound is dexamethasone, prednisolone acetate or hydrocortisone.

4. An anti-inflammatory pharmaceutical preparation comprising an effective amount of one or more inclusion compounds formed by complexing beta-cyclodextrin and an anti-inflammatory steroid compound having a molecular structure smaller than the inside dimension of the internal cavity of beta-cyclodextrin and mixed with a non-toxic pharmaceutical carrier.

5. An anti-inflammatory preparation according to claim 4 wherein said steroid compound has the general chemical structure set forth in claim 1.

6. An anti-inflammatory preparation according to claim 4 wherein said preparation is adapted to treat ocular inflammation, said carrier is an aqueous medium, said inclusion compound is dissolved in an aqueous medium and said steroid compound is dexamethasone, prednisolone acetate or hydrocortisone.

7. An anti-inflammatory preparation according to claim 6 wherein the concentration of said steroid compound is within the range of about 0.1 to about 1.0 volume %.

8. A method for preparing a water-soluble inclusion compound of a steroid compound comprising the steps of admixing in an aqueous medium beta-cyclodextrin and a steroid compound having a molecular structure smaller than the inside dimension of the internal cavity of beta-cyclodextrin.

9. A method according to claim 8 wherein the molar ratio of said steroid compound to beta-cyclodextrin is about 1:1 or less.

10. A method according to claim 9 wherein said steroid compound has the general chemical structure set forth in claim 1.

* * * * *